United States Patent [19]

Dive et al.

[11] Patent Number: 5,500,414
[45] Date of Patent: Mar. 19, 1996

[54] DERIVATIVES OF PEPTIDES USABLE AS INHIBITORS OF BACTERIAL COLLAGENASES

[75] Inventors: Vincent Dive, Vincennes; Flavio Toma, Clamart, both of France; Athanasios Yiotakis, Athens, Greece

[73] Assignee: Commissariat a l'Energie Atomique, Paris, France

[21] Appl. No.: 264,198

[22] Filed: Jun. 22, 1994

Related U.S. Application Data

[63] Continuation of Ser. No. 877,109, May 1, 1992, abandoned.

[30]     Foreign Application Priority Data

May 2, 1991 [FR] France .................. 91 05403

[51] Int. Cl.$^6$ ............ A61K 38/00; C07K 5/00; C07K 7/00; C07K 17/00
[52] U.S. Cl. .............. 514/18; 530/330; 530/331
[58] Field of Search .................. 530/330, 331; 514/18

[56]            References Cited

U.S. PATENT DOCUMENTS 4,558,034  12/1985  Galardy et al. ..................... 514/7

FOREIGN PATENT DOCUMENTS 0058427  8/1982  European Pat. Off. .
0276436  8/1988  European Pat. Off. .

OTHER PUBLICATIONS

Morrison et al., "The Behavior And Significance of Slow-Binding Enzyme Inhibitors", Adv. Enzymol. Relat. Areas Mol. Biol., (1987), pp. 201–301.
Davis et al., "A Synthetic Matrix Metalloproteinase Inhibitor Decreases Tumor Burden And Prolongs Survival Of Mice Bearing Human Ovarian Carcinoma Xenografts", Cancer Research, vol. 53, May 1993, pp. 2087–2091.
Wentworth et al., "Effect of A Metalloproteinase Inhibitor On Established Corneal Ulcers After An Alkali Burn", Investigative Ophthalmology & Visual Science, vol. 33, No. 7, Jun. 22, pp. 2174–2179.
Grenier, "Effect Of Protease Inhibitors On In Vitro Growth Of *Porphyromonas gingivalis*", Microbial Ecology in Health and Disease, vol. 5, (1992), pp. 133–138.
Dive et al. Eur. J. Biochem. 191 (1990) pp. 685–693.
Biochemistry, vol. 22, 1983, pp. 4556–4561, R. E. Galardy, et al., "Inhibition of Collagenase From *Colostridium histolyticum* By Phosphoric and Phosphonic Amides".
Biochemistry, vol. 27, 1988, pp. 4299–4304, K. A. Mookhtiar, et al., "Ketone–Substrate Analogues of Clostridium". *Histolyticum* Collagenases: "Tight-Binding Transition-State Analogue Inhibitors".
Biochemistry, vol. 28, 1989, pp. 4948–4951, D. Grobelny, et al., "Binding Energetics of Phosphorus–Containing Inhibitors of Thermolysin".

Primary Examiner—Jill Warden
Assistant Examiner—Sheela J. Huff
Attorney, Agent, or Firm—Oblon, Spivak, McClelland, Maier & Neustadt

[57]            ABSTRACT

The invention relates to novel peptide derivatives usable as inhibitors of bacterial collagenases.

These derivatives comply with the formula:

$$R^1-NH-CH(R^2)-\overset{O}{\underset{|}{P}}(OR^3)-CH_2-CH_2-CO-R^4-N(R^5)-CH(R^6)-CO-R^7 \quad (I)$$

in which $R^1$ is a hydrogen atom, a blocking group or a radical derived from an amino acid or a peptide optionally protected by a blocking group, $R^2$ is the side chain of an α-amino acid, $R^3$ is H, a metal, an alkyl or benzyl group, $R^4$ is the derivative of proline, hydroxyproline, thiazolidine or dehydroproline, $R^5$ is H or an alkyl, $R^6$ is the side of an amino acid and $R^7$ is $OR^8$ with $R^8$ being H, a metal, alkyl or benzyl, or in which $R^1$ and $R^7$ together form a divalent radical derived from an amino acid or a peptide.

The derivatives in which $R^3$ is a metal or hydrogen are usable as inhibitors of bacterial collagenases.

18 Claims, No Drawings

DERIVATIVES OF PEPTIDES USABLE AS INHIBITORS OF BACTERIAL COLLAGENASES

This application is a Continuation of application Ser. No. 07/877,109, filed on May 1, 1992, now abandoned.

The present invention relates to novel peptide derivatives usable as inhibitors of bacterial collagenases belonging to the class of zinc metalloproteases.

More specifically, it relates to polypeptide derivatives having a phosphine chelating group $PO_2$—$CH_2$ able to interact strongly with the zinc atom of the active site of said collagenases.

Collagen is a majority component of the extracellular matrix of multicellular eukaryotic organisms. Thus, it is the main constituent of the skin, tendons, bones, cartilages and tissues and represents approximately 40% of all the proteins of the human body.

Although the collagen molecule is very resistant to the action of most proteases, it can still be degraded by proteases specific thereto, i.e. collagenases.

Two distinct classes of collagenases have hitherto been identified and are characterized by the specificity of the break switch they bring about in the collagen molecule. The first class of collagenases is constituted by collagenases of higher organisms, which hydrolyze the peptide bonds containing Gly—Ile or Gly—Leu, whereas the second class is constituted by bacterial collagenases, which systematically hydrolyze all the peptide bonds having the sequence X—Gly and generally degrade any collagen molecule.

Bacterial collagenases belong to the class of zinc metalloproteases and the existence of a zinc atom in their catalytic site directly involved in the hydrolysis reaction of the peptide bond of the substrates makes it possible to develop competitive inhibitors of these enzymes. These inhibitors, which can be derivatives of peptides, have a peptide part, whose function is to carry out specific interaction with subsites of the enzyme bond, together with a chelating group able to strongly interact with the zinc atom of the active site.

This enzyme—substrate interaction model of the family of zinc proteases has recently made it possible to develop powerful inhibitors having interesting pharmacological properties. Among the latter reference can be made to the inhibitors of the conversion enzyme and inhibitors of enkephalinases. However, these compounds are not able to inhibit bacterial collagenases. This is explained by the fact that each of these three zinc proteases (enkephalinase, conversion enzyme and bacterial collagenase) has a different specificity.

In the case of bacterial collagenases, recent research has demonstrated that it was possible, in accordance with the hitherto developed hypotheses, to also produce for said class of proteases pseudo-peptide inhibitors having a thiol, ketone or phosphoramide chelating group.

Thus, Yotakis et al in Eur. J. Biochem., vol. 160, pp.413–418, 1986 and in Eur. J. Biochem., vol. 172, pp.761–766, 1988, demonstrated that the compounds HS—$CH_2$—$CH_2$—CO—Pro—Arg and HS—$CH_2$—$CH_2$—CO—Pro—Har inhibited collagenases produced by Achromobacter iophagus and by Clostridium histolyticum, the inhibition constants $K_i$ obtained being $400 \cdot 10^{-9}$M and $210 \cdot 10^{-9}$M.

Galardy et al in Biochemistry, vol. 22, no. 19, pp.4556–4561, 1983 and in U.S. Pat. No. 4,558,034 demonstrated that dipeptides and tripeptides having a phosphonyl group inhibited the collagenase of Clostridium histolyticum. In this case, for the better compound isoamyl—$PO_2$Gly—Pro—Ala, the inhibition constant $K_i$ is $20 \cdot 10^{-6}$M.

Mookhtiar et al in Biochemistry, vol.27, pp.4299–4304, 1988 demonstrated that peptide derivatives having a ketone function could inhibit the collagenases of Clostridium histolyticum. In this case, the inhibition constant $K_i$ is $1 \cdot 10^{-6}$H for the best compound (cinnamoyl—$Leu^k$—Gly—Pro—Arg).

Thus, none of the known inhibitors leads to inhibition constants of approximately 1 nanomole.

Research has also been carried out to find other more active inhibitors.

The present invention specifically relates to novel peptide derivatives which are more powerful and more selective bacterial collagenase inhibitors.

According to the invention, these peptide derivatives comply with the formula:

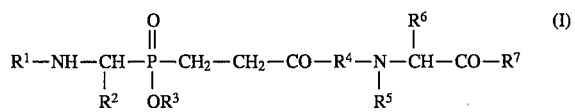

in which $R^1$ represents a hydrogen atom, a group able to block the N termination of an α-amino acid, or a radical derived from an α-amino acid or a peptide attached to NH by its termination CO and having on its N termination a hydrogen atom or a group able to block the N termination of an α-amino acid, $R^2$ is the side chain of an α-amino acid, $R^3$ is a hydrogen atom, a metal atom, a $C_1$ to $C_5$ alkyl group or a benzyl group, $R^4$ is a divalent radical derived from an α-amino acid chosen from among proline, hydroxyproline, thiazolidine and dehydroproline of formula:

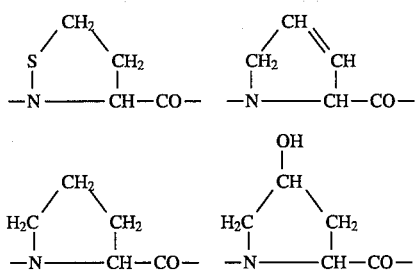

connected to CO by its nitrogen atom, $R^5$ is a hydrogen atom or a $C_1$ to $C_4$ alkyl group, $R^6$ is a $C_1$ to $C_5$ alkyl group or the side chain of an α-amino acid and $R^7$ represents $OR^8$ with $R^8$ representing a hydrogen atom, a metal atom, a $C_1$ to $C_5$ alkyl group or a benzyl group, or in which either $R^1$ and $R^7$, or $R^1$ and $R^6$, together form a divalent radical derived from an α-amino acid or a peptide having 2 to 3 amino acid residues.

In these peptide derivatives, the chemical group liable to interact with the zinc atom of the active site of the collagenases used is the phosphine group $PO_2^-$—$CH_2$, which has a high inhibiting power, whilst giving the derivative a good chemical stability.

Thus, the use of this phosphine bond makes these novel derivatives stable, particularly in an acid medium. Moreover, these derivatives are particularly interesting because, whilst having an excellent affinity with respect to bacterial collagenases, they also have a better selectivity than known inhibitors.

Moreover, the peptide derivatives according to the invention complying with formula (I) in which $R^1$ and $R^7$ together form a divalent radical derived from an α-amino acid or a peptide, have an improved stability with respect to the possible degradation by proteases.

Thus, one of the problems to be confronted when using peptides in physiological media is the fact that these molecules are very rapidly deactivated by proteases able to cleave a peptide bond present in these molecules.

In the definition of the peptides according to the invention, the term "α-amino acid" relates to the twenty α-amino acids commonly found in proteins and which are also known under the name standard amino acids and their analogs. The side chains of these amino acids comprise straight and branched alkyl, hydroxyalkyl, carboxyalkyl, aralkyl, aminoalkyl, carboxamide alkyl, mercapto alkyl, phenylalkyl, hydroxyphenyl alkyl, guanidinoalkyl, imidazoyl alkyl, indolyl alkyl and pyrrolidinyl groups.

As examples of usable amino acids, reference can be made to alanine, arginine, asparagine, aspartic acid, cysteine, glutamine, glutamic acid, glycine, histidine, isoleucine, leucine, norleucine, lysine, methionine, phenylalanine, proline, hydroxyproline, serine, threonine, tryptophan, tyrosine, valine, nitrophenyl alanine, homoarginine, thiazolidine and dehydroproline.

The terms "group able to block the N termination of an α-amine acid" or "blocking group" include all blocking groups usable for blocking the amino functions of amino acids and peptides, e.g. t-butoxycarbonyl, benzyloxycarbonyl, cinnamoyl, pivaloyl and N-(9-fluorenyl-methoxycarbonyl) groups.

The metals usable for $R^3$ and $R^8$ are in particular pharmaceutically acceptable metals, e.g. alkaline metals, such as sodium and lithium.

According to a first embodiment of the invention, $R^1$ represents a hydrogen atom, a group able to block the N termination of an α-amino acid or a radical derived from an α-amino acid or a peptide optionally protected by a blocking group and $R^7$ represents $OR^8$ with $R^8$ representing a hydrogen atom, a metal atom, an alkyl group or a benzyl group.

In these derivatives, $R^2$ is the side chain of an α-amino acid, which can e.g. be phenylalanine, and $R^4$ is derived from an amino acid chosen from among proline, hydroxyproline, thiazolidine and dehydroproline.

For $R^4$, preference is given to the use of the derivative of proline of formula:

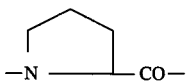

In these derivatives, the termination

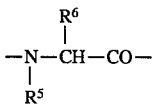

can correspond to different amino acids. For example, it can be norleucine and in this case $R^5$ is a hydrogen atom and $R^6$ is the n-butyl group.

In this first embodiment of the invention, $R^1$ can represent a blocking group, e.g. the benzyloxycarbonyl group, or can correspond to a protected amino acid residue, e.g. to glycine protected by a blocking group, or to a protected peptide residue, e.g. —Pro—Gly protected by a blocking group. This blocking group can also be the benzyloxycarbonyl group.

When the peptide derivatives according to the invention are intended for use as bacterial collagenase inhibitors, $R^3$ is preferably a metal such as sodium and in $R^7$, i.e. $OR^8$, $R^8$ is also preferably a metal, e.g. sodium.

According to a second embodiment of the invention, the peptide derivative is a cyclopeptide e.g. corresponding to the formula:

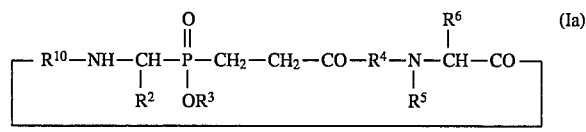

in which $R^{10}$ represents a divalent radical derived from a peptide or an α-amino acid.

Generally $R^{10}$ is derived from a peptide and e.g. has two amino acid residues. With such a $R^{10}$, a cyclic derivative is obtained which is more resistant to degradation by proteases than the non-cyclic formula I derivatives, which also keeps intact its inhibiting properties with respect to bacterial collagenases.

In this second embodiment of the invention, $R^2$, $R^3$, $R^4$, $R^5$ and $R^6$ advantageously represent the same groups as in the first embodiment of the invention.

The peptide derivatives according to the invention can be prepared by conventional processes.

Thus, the derivatives corresponding to the first embodiment of the invention, in which $R^1$ is a blocking group, $R^2$, $R^3$, $R^4$, $R^5$ and $R^6$ have the meanings given hereinbefore, and $R^7$ represents $OR^8$ with $R^8$ identical to $R^3$, can be prepared by a process having the following stages:

a) reacting an aldehyde of formula $R^2$—CHO, in which $R^2$ has the meaning given hereinbefore with diphenyl aminohypophosphite for obtaining a diphenyl methylaminoalkylphosphinic acid of formula:

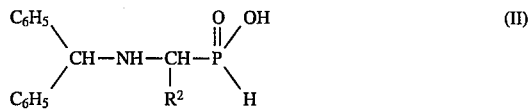

b) reacting the diphenyl methylaminoalkylphosphinic acid of formula (II) with a halogenated hydracid of formula HX, in which X is a halogen atom, to obtain an amino alkyl phosphinic acid of formula:

c) protecting the N termination of the aminoalkylphosphinic acid of formula (III) by the blocking group $R^1$ to obtain the aminoalkylphosphinic acid of formula:

d) reacting the acid of formula (IV) with an alkyl acrylate of formula:

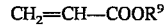

in which $R^9$ is an alkyl radical to obtain the compound of formula:

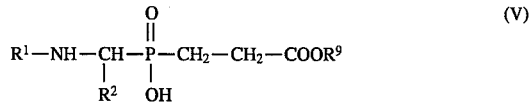

e) saponifying the compound of formula (V) to obtain the acid of formula (VI)

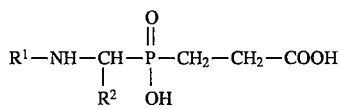  (VI)

f) reacting the acid of formula (VI) with a peptide of formula:

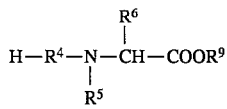

in which $R^9$ is an alkyl radical to obtain the peptide of formula VII

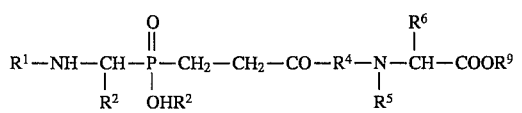  (VII)

g) reacting the peptide of formula (VII) with a halide of formula $R^3X$, in which $R^3$ has the meaning given hereinbefore and X is a halogen atom for obtaining the peptide of formula (I).

The peptide derivatives corresponding to the first embodiment of the invention, i.e. complying with formula (I), in which $R^1$ is a radical derived from an amino acid or a peptide, whose N termination is protected by a blocking group, $R^2$, $R^3$, $R^4$, $R^5$ and $R^6$ have the meanings given hereinbefore, and $R^7$ represents $OR^8$ with $R^8$ identical to $R^3$, can be prepared by a process having the following successive stages:

a') preparing a peptide of formula (VII) carrying out stages a) to f) of the process described hereinbefore, b') eliminating the protective group $R^1$ of the peptide of formula (VII) to obtain the peptide of formula:

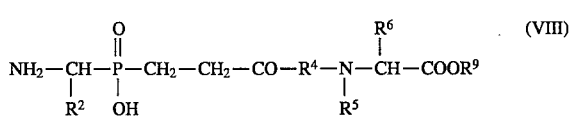  (VIII)

c') reacting the peptide of formula (VIII) with an amino acid or a peptide, whose N termination is protected by a blocking group and whose C termination is activated by a nitrophenyl group and d') reacting the peptide obtained in stage c') with a halide of formula $R^3X$, in which X is a halogen atom.

The cyclopeptide derivatives corresponding to the second embodiment of the invention and complying with formula:

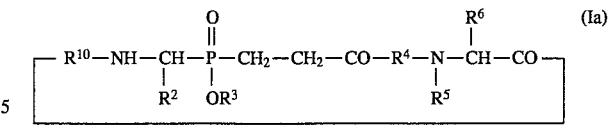  (Ia)

in which $R^{10}$ represents a divalent radical derived from a peptide or an amino acid and $R^2$, $R^3$, $R^4$, $R^5$ and $R^6$ have the meanings given hereinbefore, can be prepared by a process having the following successive stages:

a") preparing a peptide of formula (VII) carrying out stages a) to f) of the process described hereinbefore, b") eliminating the protective group $R^1$ of the peptide of formula (VII) to obtain the peptide of formula:

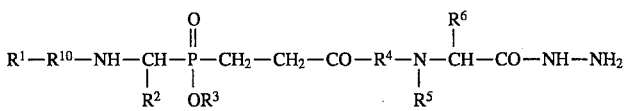  (VIII)

c") reacting the peptide of formula (VIII) with a peptide of formula $R^1$—$R^{10}$—$OR^{11}$, in which $R^1$ is a blocking group of the N termination of the peptide and $R^{11}$ is a nitrophenyl group, to obtain the peptide of formula:

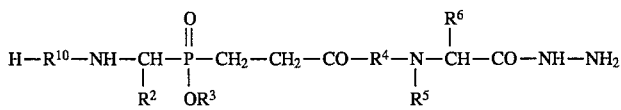  (IX)

d") reacting the peptide of formula (IX) with hydrazine to obtain the hydrazide of formula:

$$R^1-R^{10}-NH-CH-\underset{\underset{OR^3}{|}}{\overset{\overset{O}{\|}}{P}}-CH_2-CH_2-CO-R^4-N-\underset{R^5}{\overset{R^6}{|}}CH-CO-NH-NH_2 \quad (X)$$

e") deprotecting the hydrazide of formula (X) to obtain the hydrazide of formula:

$$H-R^{10}-NH-CH-\underset{\underset{OR^3}{|}}{\overset{\overset{O}{\|}}{P}}-CH_2-CH_2-CO-R^4-N-\underset{R^5}{\overset{R^6}{|}}CH-CO-NH-NH_2 \quad (XI)$$

f") cyclizing the hydrazide of formula (XI) to obtain the cyclopeptide of formula (Ia)

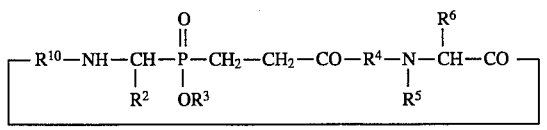  (Ia)

In the processes described hereinbefore, the different stages are carried out by technical processes using reagents and solvents generally used in peptide chemistry for carrying out these reaction types. The peptide derivatives according to the invention can have numerous different applications due to their inhibiting power with respect to bacterial collagenases. They can in particular be used in pharmaceutical compositions intended for the treatment of certain infections due to the presence of bacteria able to excrete collagenase.

Thus, the presence of such bacteria can lead to a significant destruction of collagen and can therefore attack the integrity of the conjunctive tissue of the infected organism. This is in particular the case with infections by *Clostridium histolyticum* or *Pseudomonas aeruginosa*. They can be in particular used for the treatment of parodontal ailments associated with collagenolytic microorganisms responsible for the destruction of collagen, e.g. entering the composition of the gums. Thus, although the peptide derivatives according to the invention do not have a direction action on the collagenolytic microorganisms, they constitute an interesting therapeutic means in certain pathologies (e.g. gangrene and dental infections), because they are powerful, specific inhibitors of bacterial collagenases. In these pharmaceutical applications, it is also possible to use the inventive peptide derivatives for inhibiting other metalloproteases having specificities close to those of bacterial collagenases involved in the metabolism of collagen.

The invention also relates to a pharmaceutical composition incorporating a pharmaceutically effective quantity of a peptide derivative according to the invention complying with formula (I) given hereinbefore, in which $R^3$ is a hydrogen or metal atom.

This composition can be in the form of a physiologically acceptable salt of the peptide derivative, in a vehicle or an appropriate physiologically acceptable support. It can e.g. be administered in the form of solutions or suspensions by injection. The preferred doses for administration are in the range 1 to approximately 5 mg/kg/day.

The compositions can also be in the form of those intended for oral administration, such as tablets or capsules, e.g. obtained by combining the peptide derivatives according to the invention with supports, excipients and additives of a conventional nature such as magnesium carbonate, magnesium stearate, talc, sugar, lactose, peptin, dextrin, starch, gelatin, tragacanth, methyl cellulose, sodium carboxymethyl cellulose, cacao butter, etc. Diluents, flavouring agents, solubilizers, lubricants, suspending agents, binders, disintegrating agents, etc. can be added to the compositions. The active ingredients can also be encapsulated with other supports, etc.

The peptide derivatives according to the invention can also be used in other fields, e.g. for the protection of skins in the production of leather and for the protection of gelatin in different activities using this product.

Thus, although the natural substrate of bacterial collagenases would appear to be mainly native collagen, it is known that this protease can use as the substrate collagen in its denatured form, i.e. gelatin. Gelatin is at present used in various fields and it is of interest to maintain the perfect integrity of gelatin for these applications. This can be obtained by using the peptide derivatives according to the invention as competitive inhibitors of bacterial collagenases liable to destroy gelatin.

It is also possible to use the peptide derivatives according to the invention for isolating novel zinc proteases having a specificity close to that of bacterial collagenases, particularly within higher organisms. In this case, it is possible to use the peptide derivatives according to the invention as a ligand for producing affinity columns with a view to separating with respect to other zinc proteases.

It is also possible to use the peptide derivatives according to the invention for controlling the activity of bacterial collagenase, e.g. in biotechnological processes based on the use of collagenolitic bacteria, e.g. for the tenderizing of meat and the digestion of sediments in sedimentation tanks.

Other characteristics and advantages of the invention can be gathered from the following illustrative, nonlimitive examples.

EXAMPLE 1

Preparation of
Z—D,LPhe*—PO$_2$CH$_2$—CH$_2$—CO—Pro—Nle*,2Na$^+$
(Compound A)

(Z = C$_6$H$_5$—CH$_2$—OCO,

Phe* = —NH—CH(CH$_2$C$_6$H$_5$) and

Nle° = NH—CH—COO)
　　　　|
　　　(CH$_2$)$_3$
　　　　|
　　　　CH$_3$ a) Synthesis of D,L diphenylmethylamino-1-phenyl-2-ethyl phosphinic acid (1) (compound 1):

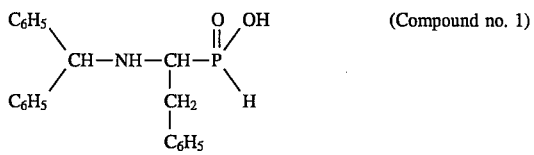

(Compound no. 1)

A dioxan solution (12 ml) containing phenyl acetaldehyde (12 g, 0.1 mole) is gently added to a dioxan solution (300 ml) containing in suspension diphenyl aminohypophosphite (24.9 g, 0.1 mole). Phenyl acetaldehyde addition takes place at 100° C. under a nitrogen atmosphere in such a gradual manner that the temperature does not exceed 100° C. and takes 3 hours. The water formed during the reaction is eliminated by azeotropic distillation. After adding all the aldehyde, the reaction is left under reflux for 15 minutes. This mixture is cooled and then diluted with 100 ml of ethanol. The crystalline product is filtered, washed with ethanol, then ether and then dried. This gives 12 g of compound 1 (34%); (m.p.=210° C., RF(1)=0.81).

b) Synthesis of D,L amino-1-phenyl-2-ethyl phosphinic acid (2) of formula:

(Compound no. 2)

Compound 1 (3.51 g, 10 mmole) is heated to 100° C. for 1 h in a 48% HBr/H$_2$O mixture (12 ml). This mixture is evaporated to dryness under a very high vacuum and then the product is taken up by water. The diphenyl methyl bromide is extracted from said solution by an ether treatment. After evaporation, the product is taken up in 30 ml of ethanol. This mixture, to which is added 1 ml of propylene oxide, is cooled to 4° C. up to a complete precipitation of the product has taken place. The filtered product is washed with ethanol, then ether, followed by drying. The expected compound 2 is obtained with a 76% yield (1.42 g), RF(1)=0.37, RF(2)=0.7, m.p. 226° C.

c) Synthesis of the D,L benzyloxycarbonylamino-1-phenyl-2-ethyl phosphinic acid (3) of formula:

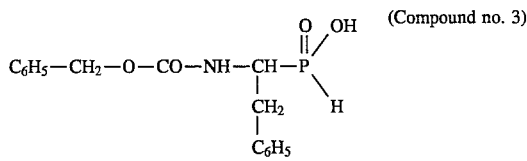
(Compound no. 3)

Compound 2 (1.1 g, 6 mmole) is dissolved in 10 ml of water and then the pH of this solution is adjusted to 9.5 with the aid of a 4N soda solution. To this mixture cooled in an icebath is gently added benzylchloroformate (1.2 ml, 7.5 mmole), whilst maintaining the pH of the reaction at 9.5 by successive soda additions. Stirring of the reaction mixture is maintained at 0° C. for 30 min. and then for 1 h at ambient temperature. After diethyl ether treatment, the mixture is cooled, and then acidified by the addition of hydrochloric acid. The product which precipitates is filtered, washed with cold water and dried. The expected compound 3 is obtained with a 76% yield (1.5 g), RF(1)=0.57, RF(2)=0.76, m.p. 110° C.

d) Synthesis of ethyl D,L-(benzyloxycarbonylamino-1'-phenyl-2')-hydroxyphosphinylethyl-3-propionate (4) of formula:

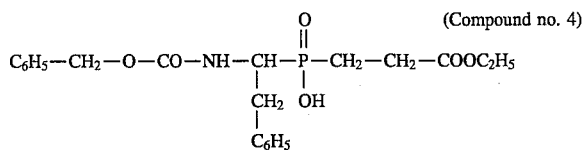
(Compound no. 4)

A suspension of compound 3 (1.27 g, 4 mmole) in hexamethyl disilazane (0.968 g, 6 mmole) is heated, accompanied by stirring, at 110° C. for 40 min. and under a nitrogen atmosphere. After cooling this mixture to 90° C., there is a dropwise addition of ethyl acrylate (0.48 g, 4.8 mmole). This reaction is then left at 90° C., for 15 min. and under stirring. 12 ml of absolute ethanol are added to the said mixture when its temperature reaches 70° C. and then once the temperature has returned to ambient, evaporation to dryness takes place. The residue is dissolved in 10 ml of 10% NaHCO$_3$ and then washed with diethyl ether. Once the aqueous solution has been cooled it is acidified to pH 1.5 with 1N HCl. The precipitate is filtered, washed with cold water and dried. The expected compound 4 is obtained with an 84% yield (1.4 g), RF(1)=0.52, RF(3)=0.8.

e) Synthesis of benzyloxycarbonylamino-1'-phenyl-2'-hydroxyphosphinylethyl-3-propionic acid of formula:

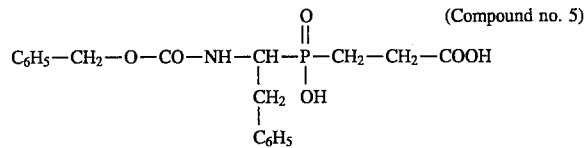
(Compound no. 5)

Compound 4 (1.26 g, 3mmole) is dissolved in 6.5 ml of 1N KOH and left under stirring at ambient temperature for 45 min. This mixture is then acidified to pH 1.5 with 1N HCl. The precipitate is extracted with ethyl acetate and then this phase is washed with an aqueous solution saturated with NaCl, dried with sodium sulphate and concentrated in a small volume. After one night at 4° C., the precipitate is filtered, washed with a little ethyl acetate and dried. The expected compound 5 is obtained with an 88% yield (1 g), RF(1)=0.51, RF(2)=0.93, RF(3)=0.55, RF(5)=0.41.

f) Synthesis of the peptide of formula:

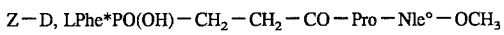

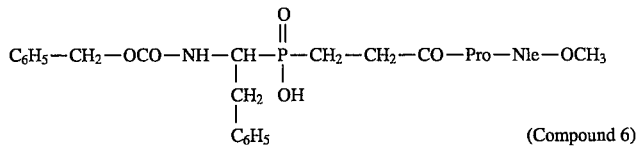
(Compound 6)

To a cold solution at 4° C. of compound 5 dissolved in tetrahydrofuran (12 ml) is added 1.1-carbonyldiimidazole (1.78 g, 11 mmole). After 45 min. stirring at ambient temperature, to the said mixture is added the peptide Pro—Nle—OCH$_3$ (5.5 mmole) diluted in tetrahydrofuran (5 ml). After 24 h under stirring, the mixture is evaporated to dryness. This residue is dissolved in 20 ml of 0.27N KOH (5.5 mmole) and said phase is immediately washed with diethyl ether, followed by acidification to pH 1.5 with 1N HCl. The product which precipitates is taken up in ethyl acetate and this phase is washed with water, dried with sodium sulphate and concentrated to dryness. This residue is dissolved in a small chloroform volume and then precipitated by adding petroleum ether. The final compound 6, after filtration, washing and drying, is obtained with an 89% yield (3 g). RF(5)=0.6, RF(6)=0.33.

g) Synthesis of the peptide of formula:

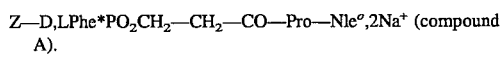

Compound 6, (0.15 g, 0.19 mmole) is dissolved in 10% ethanol (15 ml), followed by the addition of 2N KOH (0.475 ml) accompanied by stirring for 3 h at ambient temperature. The aqueous phase is acidified to pH 1.5 with 1N HCl. The precipitate is taken up in ethyl acetate and the organic phase is washed with an aqueous saturated NaCl solution, dried with sodium sulphate and concentrated to dryness. The residue is diluted in an aqueous solution containing NaHCO$_3$ (0.3 mmole), followed by lyophilization. The expected product is obtained with a 93% yield. RF(1)=0.27, RF(2)=0.85, RF(8)=0.57.

$^1$H NMR (H$_2$O): CH$_\epsilon$Nle 0.94; CH$_{\delta,\gamma}$Nle 1.37 (m, 4); CH$_\beta$Nle 1.84 (m, 1); CH$_\beta$Nle 1.73 (m, 1); CH$_\alpha$Nle 4.18 (m, 1); NHNle 8.08 (d,1); CH$_\gamma$Pro 2.02 (m, 2); CH$_\beta$Pro 2.02 (m, 1); CH$_\beta$Pro 2.28 (m, 1); CH$_\delta$Pro 3.63 (m, 1); CH$_\delta$Pro 3.48 (m, 1); CH$_\alpha$Pro 4.41 (q, 1); P—CH$_2$—CH$_2$ 2.57 (m,2); P—CH$_2$—CH$_2$ 1.88 (m,2); CH$_\beta$Phe 2.73 (m,1); CH$_\beta$Phe 3.26 (m,1); CH$_\alpha$Phe 3.96 (m,1); NHPhe 7.26; (d,1); Z—CH$_2$— 5 (m,2); Ar 7.35 (m, 10).

$^{31}$P NMR (H$_2$O): 43.83

EXAMPLE 2

Preparation of the peptide

Z—Pro—Phe*—PO(OH)—CH$_2$—CH$_2$—CO—Pro—Nle* 2Na$^+$ (Compound B)

(Z=C$_6$H$_5$OCO— and Phe*=—NH—CH(CH$_2$C$_6$H$_5$)—)

The protective group Z of compound 6 is eliminated by conventional catalytic hydrogenolysis. The product obtained is coupled with Z—Pro—ONph (nitrophenyl ester) of a commercial nature in dimethylformamide. The product is saponified and then treated under the same conditions as those described for obtaining compound A.

$^1$H NMR (H$_2$O): CH$_\epsilon$Nle 0.89; CH$_{\delta,\gamma}$Nle 1.35 (m, 4); CH$_\beta$Nle 1.84 (m, 1); CH$_\beta$Nle 1.73(m, 1); CH$_\alpha$Nle 4.12 (m, 1); NHNle 7.96 (d,1); CH$_\gamma$Pro 2.02(m, 2); CH$_\beta$Pro 1.98 (m, 1); CH$_\beta$Pro 2.25 (m, 1); CH$_\delta$Pro 3.63 (m, 1); CH$_\delta$Pro 3.52(m, 1); CH$_\alpha$Pro 4.28 (q, 1); P—CH$_2$—CH$_2$ 2.63 (m,2); P—CH$_2$—CH$_2$ 1.70 (m,2); CH$_\beta$Phe 2.73 (m, 1); CH$_\beta$Phe 3.31 (m,1); CH$_\alpha$Phe 4.42 (m,1); NHPhe 8.16 (d,1); CH$_\gamma$Pro 1.55 (m, 2); CH$_\beta$Pro 1.72 (m, 1); CH$_\beta$Pro 2.15 (m, 1); CH$_\delta$Pro 3.42 (m, 1); CH$_\alpha$Pro 4.32 (q, 1); Z—CH$_2$— 5 (m,2); Ar 7.35–7.45 (m, 10).

$^{31}$P NMR (H$_2$O): 43.2

EXAMPLE 3

Preparation of the peptide

Z—Gly—Pro—Phe*—PO(OH)—CH$_2$—CH$_2$—CO—Pro—Nle*2Na$^+$ (compound C)

(Z=C$_6$H$_5$OCO and Phe*=—NH—CH(CH$_2$C$_6$H$_5$)—)

The synthesis of this peptide is carried out by coupling Z—Gly—Pro—ONph to compound 6, which has previously undergone conventional catalytic hydrogenolysis, followed by treatment under the same conditions as those described for obtaining compound A.

$^1$H NMR (H$_2$O): CH$_\epsilon$Nle 0.89; CH$_{\delta,\gamma}$Nle 1.35 (m, 4); CH$_\beta$Nle 1.84 (m, 1); CH$_\beta$Nle 1.73(m, 1); CH$_\alpha$Nle 4.12 (m, 1); NHNle 7.96 (d,1); CH$_\gamma$Pro 2.02(m, 2); CH$_\beta$Pro 1.98 (m, 1); CH$_\beta$Pro 2.25 (m, 1); CH$_\delta$Pro 3.63 (m, 1); CH$_\delta$Pro 3.52(m, 1); CH$_\alpha$Pro 4.28 (q, 1); P—CH$_2$—CH$_2$ 2.63 (m,2); P—CH$_2$—CH$_2$ 1.70 (m,2); CH$_\alpha$Gly 3.65 (d,1); CH$_\alpha$Gly 3.45 (d,1); CH$_\beta$Phe 2.73 (m, 1); CH$_\beta$Phe 3.31 (m,1); CH$_\alpha$Phe 4.37(m,1); NHPhe 8.2 (d,1); CH$_\gamma$Pro 1.55 (m, 2); CH$_\beta$Pro 1.70 (m, 1); CH$_\beta$Pro 2.15 (m, 1); CH$_\delta$Pro 3.40 (m, 1); CH$_\alpha$Pro 4.29(q, 1); Z—CH$_2$— 5 (m,2); Ar 7.35–7.45 (m, 10).

$^{31}$P NMR (H$_2$O): 43.35

EXAMPLE 4

Preparation of the cyclopeptide

Gly—Pro—Phe*—PO(OH)—CH$_2$—CH$_2$—CO—Pro—Nle°, Na$^+$
(cyclic)

The synthesis of this product takes place from the compound Z—Gly—Pro—Phe*—PO(OH)—CH$_2$—CH$_2$—CO—Pro—Nle°—OCH$_3$ obtained in example 3 during the synthesis of compound C. The hydrazide of this compound is prepared by hydrazine treatment in methanol and then the protective group Z is eliminated by conventional catalytic hydrogenation. Cyclization is then carried out according to the method of Bodanzsky M. and Henes G. B., 1975, Bioorg. Chem., vol.4, pp.212–218.

$^1$H NMR (H$_2$O): CH$_\epsilon$Nle 0.92; CH$_\delta$Nle 1.28 (m, 2); CH$_\gamma$Nle 1.28 (m,2); CH$_\beta$Nle 1.95 (m, 1); CH$_\beta$Nle 1.67(m, 1); CH$_\alpha$Nle 4.5 (m, 1); NHNle 8.31 (d,1); CH$_\gamma$Pro 2.11 (m, 2); CH$_\beta$Pro 2.02 (m, 1); CH$_\beta$Pro 2.38 (m, 1); CH$_\delta$Pro 3.63 (m, 1); CH$_\delta$Pro 3.82(m, 1); CH$_\alpha$Pro 4.38 (q, 1); P—CH$_2$—CH$_2$ 2.68 (m,2); P—CH$_2$—CH$_2$ 1.62 (m,1); P—CH$_2$—CH$_2$ 2.29 (m, 1); CH$_\beta$ Phe 2.78 (m,1); CH$_\beta$Phe 3.25 (m,1); CH$_\alpha$Phe 4.27 (m,1); NHPhe 8.33 (d,1); CH$_\gamma$Pro 1.88 (m, 2); CH$_\beta$Pro 1.18 (m, 1); CH$_\beta$Pro 2.06(m, 1); CH$_\delta$Pro 3.58 (m, 1); CH$_\delta$Pro 3.41 (m, 1) CH$_\alpha$Pro 4.28 (q, 1); Ar 7.35–7.45 (m, 10).

$^{31}$P NMR (H$_2$O): 43.83

EXAMPLE 5

Determination of the activity of the inhibitors

The activities of the different compounds A, B, C and D were determined on the one hand by measuring the association rate constant of the inhibitors to collagenase by the method of Morrison, J. & Walsh, C. T., 1987, Adv., Enzymol. Relat. Aeras Mol. Biol. applied in the case where the inhibitors are of the slow binding type and on the other hand by measuring the dissociation rate constants of the inhibitors of the enzyme—inhibitor complex. In this case, after allowing the collagenase to preincubate in the presence of an inhibitor excess, the thus formed enzyme—inhibitor complex is purified by gel filtration. The solution containing the purified complex is then diluted by a factor of 10,000 in a reference buffer and then, as a function of time, measurement takes place of the return of the activity of the collagenase, which represents the dissociation of the inhibitor of the enzyme—inhibitor complex.

The inhibition constants given in the table correspond to the ratio of the dissociation rate constants Koff and the association rate constants Kon measured in this way. In all the activity measurement experiments we used as the synthetic substrate Fa—Leu—Gly—Pro—Ala in a pH7 Tricine buffer. The source of the bacterial collagenase used was the strain *Empedobacterium collagenolyticum*.

For comparison, we determined in the same way the activity of the following compounds:

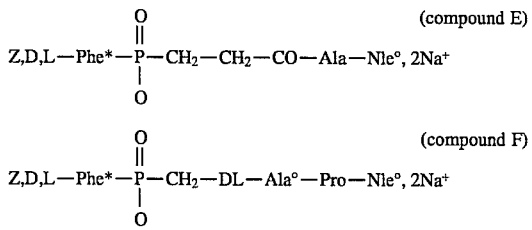

(compound E)

(compound F)

(compound D)

which were prepared in the same way as compound A by using for compound E in stage f) the peptide Ala—Nle—OCH$_3$ instead of Pro—Nle—OCH$_3$ and for compound F in stage d) ethyl methacrylate instead of ethyl acrylate.

On the basis of the results in the following table, it can be seen that the replacement in compound A of Pro by an amino acid not belonging to the group of hydroxyproline, thiazolidine and dehydroproline greatly reduces the activity of the compound with respect to bacterial collagenases. In the same way, the replacement of glycine by alanine leads to poor results.

TABLE

| Compound | Formula | Inhibition Constants Ki(nM) |
|---|---|---|
| A | Z,D,L-Phe*—P(=O)(O⁻)—CH₂—CH₂—CO—Pro—Nle°, 2Na⁺ | 12 |
| B | Z—Pro—D,L-Phe*—P(=O)(O⁻)—CH₂—CH₂—CO—Pro—Nle°, 2Na⁺ | 80 |
| C | Z—Gly—Pro—D,L-Phe*—P(=O)(O⁻)—CH₂—CH₂—CO—Pro—Nle°, 2Na⁺ | 0.4 |
| D | Gly—Pro—D,L-Phe*—P(=O)(O⁻)—CH₂—CH₂—CO—Pro—Nle°, Na⁺ | 8 |
| E | Z,D,L-Phe*—P(=O)(O⁻)—CH₂—CH₂—CO—Ala—Nle°, 2Na⁺ | 1000 |
| F | Z,D,L-Phe*—P—CH₂—DL-Ala°—Pro—Nle°, 2Na⁺ | 2350 |

$$\text{Phe*} = -NH-CH(-CH_2-C_6H_5)-$$
$$\text{Nle°} = -NH-CH(-CH_2-C_6H_5)-COO^-$$
$$\text{Ala°} = -CH(CH_3)-CO-$$
$$Z = C_6H_5CH_2OCO$$

We claim:

1. A peptide derivative of the formula $$R^1-NH-CH(R^2)-\overset{O}{\overset{\|}{P}}(OR^3)-CH_2-CH_2-CO-R^4-N(R^5)-CH(R^6)-CO-R^7 \quad (I)$$

wherein

R¹ represents a t-butoxycarbonyl group, a benzyloxycarbonyl group, a cinnamoyl group, a pivaloyl group, a N-9-fluorenylmethoxycarbonyl group, or a group obtained by removing OH from the carboxy terminus of an amino acid or dipeptide whose amino terminus is blocked by a t-butoxycarbonyl group, a benzyloxycarbonyl group, a cinnamoyl group, a pivaloyl group or a N-9-fluorenylmethoxycarbonyl group, R² is the side chain of an α-amino acid, R³ is a hydrogen atom or a metal atom, R⁴ is a divalent radical derived from an α-amino acid selected from the group consisting of proline, hydroxyproline, thiazolidine and dehydroproline of formula:

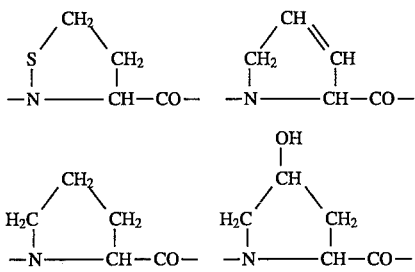

connected to CO by its nitrogen atom,

R⁵ is a hydrogen atom,

R⁶ is a C₁ to C₅ alkyl group and

R⁷ represents OR⁸ with R⁸ representing a hydrogen atom or a metal atom.

2. Peptide derivative according to claim 1, wherein R⁴ represents the radical of formula:

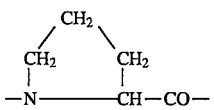

3. Peptide derivative according to claim 1, wherein $R^5$ is a hydrogen atom and $R^6$ is a n-butyl group.

4. Peptide derivative according to claim 1, wherein $R^2$ represents a phenyl methyl radical.

5. The peptide derivative according to claim 1, wherein $R^1$ represents a t-butoxycarbonyl group, a benzyloxycarbonyl group, a cinnamoyl group, a pivaloyl group or a N-9-fluorenylmethoxycarbonyl group.

6. Peptide derivative according to claim 5, wherein $R^1$ is the benzyloxycarbonyl group.

7. The peptide derivative according to claim 1, wherein $R^1$ represents proline with its N terminus blocked with a member selected from the group consisting of a t-butoxycarbonyl group, a benzyloxycarbonyl group, a cinnamoyl group, a pivaloyl group, a N-9-fluorenylmethoxycarbonyl group.

8. Peptide derivative according to claim 1, wherein $R^1$ represents the radical derived from a peptide Pro—Gly protected on the N termination of Gly by a blocking group.

9. Peptide derivative according to claim 8, wherein the blocking group is the benzyloxycarbonyl group.

10. Peptide derivative according to claim 1, wherein $R^7$ represents $OR^8$ with $R^8$ representing a sodium atom and $R^3$ representing a sodium atom.

11. Peptide derivative according to claim 1, wherein $R^2$ represents a phenylmethyl group, $R^3$ a sodium atom, $R^4$ Pro, $R^5$ a hydrogen atom, $R^6$ the n-butyl group and $R^7$ ONa.

12. Peptide derivative according to claim 11, wherein $R^1$ represents the benzyloxycarbonyl group.

13. Peptide derivative according to claim 11, wherein $R^1$ represents a $C_6H_5$—$CH_2$—O—CO—Pro.

14. Peptide derivative according to claim 11, wherein $R^1$ represents a $C_6H_5$—$CH_2$—O—CO—Gly—Pro—.

15. Peptide derivative according to claim 1, wherein $R^2$ represents a phenylmethyl group, $R^3$ Na, $R^4$ Pro, $R^5$ a hydrogen atom, $R^6$ a n-butyl group and $R^1$ and $R^7$ together form the —Pro—Gly— radical.

16. A pharmaceutical composition which inhibits bacterial collagenases, comprising a pharmaceutically effective quantity of a peptide derivative of the formula:

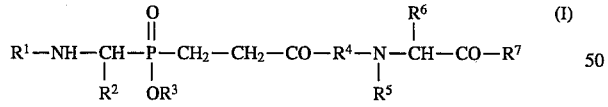

wherein $R^1$ represents a hydrogen atom, a t-butoxycarbonyl group, a benzyloxycarbonyl group, a cinnamoyl group, a pivaloyl group, a N-9-fluorenylmethoxycarbonyl group, or a group obtained by removing OH from the carboxy terminus of an unprotected amino acid or a group obtained by removing OH from the carboxy terminus of an amino acid whose amino terminus is blocked by a t-butoxycarbonyl group, a benzyloxycarbonyl group, a cinnamoyl group, a pivaloyl group or a N-9-fluorenylmethoxycarbonyl group, $R^2$ is the side chain of an α-amino acid, and $R^3$ is an alkaline metal or hydrogen atom $R^4$ is a divalent radical derived from an α-amino acid selected from the group consisting of proline, hydroxyproline, thiazolidine and dehydroproline of formula:

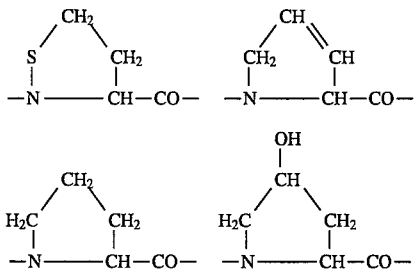

connected to CO by its nitrogen atom, $R^5$ is a hydrogen atom or a $C_1$ to $C_4$ alkyl group, $R^6$ is a $C_1$ to $C_5$ alkyl group or the side chain of an α-amino acid and $R^7$ represents $OR^8$ with $R^8$ representing a hydrogen atom, an alkaline metal atom, a $C_1$ to $C_5$ alkyl group or a benzyl group, or in which either $R^1$ and $R^7$, or $R^1$ and $R^6$, together form a divalent radical derived from an α-amino acid or a peptide having 2 to 3 amino acid residues.

17. The pharmaceutical composition according to claim 16, wherein said pharmaceutically effective quantity is in the range of approximately 1 to 5 mg/kg/day.

18. The pharmaceutical composition according to claim 16, wherein said alkaline metal is lithium or sodium.

* * * * *